United States Patent
Gokhale et al.

(10) Patent No.: US 10,246,449 B2
(45) Date of Patent: Apr. 2, 2019

(54) 1,2,3 TRIAZOLE-THIAZOLE COMPOUNDS, PROCESS FOR PREPARATION AND USE THEREOF

(71) Applicant: Council of Scientific & Industrial Research, New Delhi (IN)

(72) Inventors: Rajesh Sudhir Gokhale, New Delhi (IN); Dumbala Srinivasa Reddy, Maharashtra (IN); Balamkundu Seetharamsingh, Maharashtra (IN); Parul Ganju, New Delhi (IN); Vivek Tirunelveli Natarajan, New Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/064,415

(22) PCT Filed: Dec. 20, 2016

(86) PCT No.: PCT/IN2016/050449
§ 371 (c)(1),
(2) Date: Jun. 20, 2018

(87) PCT Pub. No.: WO2017/109793
PCT Pub. Date: Jun. 29, 2017

(65) Prior Publication Data
US 2018/0370962 A1 Dec. 27, 2018

(30) Foreign Application Priority Data
Dec. 21, 2015 (IN) .............. 4189/DEL/2015

(51) Int. Cl.
*C07D 417/06* (2006.01)
*A61P 17/00* (2006.01)
(52) U.S. Cl.
CPC ............ *C07D 417/06* (2013.01); *A61P 17/00* (2018.01)

(58) Field of Classification Search
CPC ............................... C07D 417/06; A61P 17/00
See application file for complete search history.

(56) References Cited

U.S. PATENT DOCUMENTS

| 7,259,262 B2 * | 8/2007 | Bossennnaier ...... C07D 413/14 548/202 |
| 8,927,736 B2 | 1/2015 | Hein et al. | |

FOREIGN PATENT DOCUMENTS

| WO | WO 02/42298 A1 | 5/2002 |
| WO | WO 2007/030559 A2 | 3/2007 |
| WO | WO 2007/087427 A2 | 8/2007 |
| WO | WO 2011/042797 A1 | 4/2011 |
| WO | WO 2015/101957 A1 | 7/2015 |

OTHER PUBLICATIONS

Pokhodylo, N. T. et al. 2009 "Synthesis of 1H-1,2,3-Triazole Derivatives by the Cyclization of Aryl Azides With 2-Benzothiazolylacetonone, 1,3-Benzo-Thiazol-2-Ylacetonitrile, and (4-Aryl-1,3-Thiazol-2-Yl)Acetonitriles" *Chemistry of Heterocyclic Compounds* 45: 483-488.
Pokhodylo, N.T. et al. 2010 "Synthesis of 2-Azido-1,3-Thiazoles As 1,2,3-Triazole Precursors" *Synthetic Communications* 40: 391-399.
Zhang, Y. et al. 2014 "Oxidative Stress—Induced Calreticulin Expression and Translocation: New Insights into the Destruction of Melanocytes" *Journal of Investigative Dermatology* 134: 183-191.

* cited by examiner

*Primary Examiner* — Golam M Shameem
(74) *Attorney, Agent, or Firm* — Knobbe, Martens, Olson & Bear, LLP

(57) ABSTRACT

A 1,2,3 triazole-thiazole compound of formula (I) or pharmaceutically acceptable salt thereof, process for its preparation, its pharmaceutical composition and method for the treatment for stalling vitiligo spread or provide prophylactic benefit to individuals with vitiligo predisposition.

13 Claims, 1 Drawing Sheet

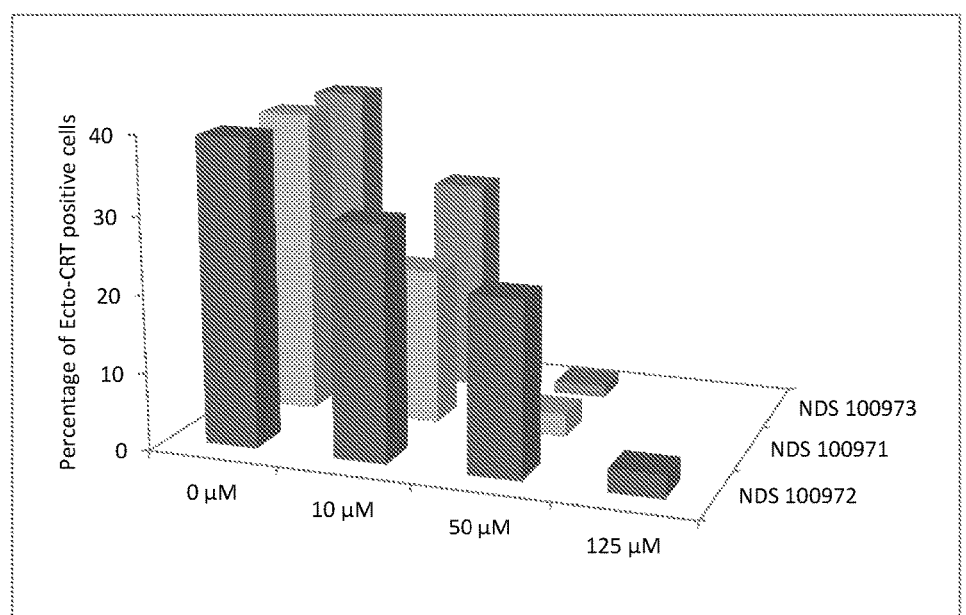

1,2,3 TRIAZOLE-THIAZOLE COMPOUNDS, PROCESS FOR PREPARATION AND USE THEREOF

FIELD OF THE INVENTION

The present invention relates to novel 1,2,3 triazole-thiazole compounds of formula (I). More particularly, the present invention relates to novel 1,2,3 triazole-thiazole compounds of formula (I) or pharmaceutically acceptable salt thereof, process for its preparation, its pharmaceutical composition and method to target the mechanisms that sustain autoimmune reactions and thus provide new treatment options for stalling vitiligo spread or provide prophylactic benefit to individuals with vitiligo predisposition using compound of formula (I).

BACKGROUND AND PRIOR ART

Vitiligo is a chronic depigmenting disorder that is manifested by the sudden appearance of white patches on skin. Depigmentation of entire skin in vitiligo follows a variable and often unpredictable course. While the prevalence of vitiligo varies from 0.5-2% in the world, the disease is of major concern in India, where it is considered as a major social stigma. The disfigurement caused by the disease has profound effects on the quality of life of the individual, with subjects feeling distressed and isolated. Depigmentation in vitiligo is considered a consequence of melanocyte disappearance from the basal layer of skin. However, very rarely non-functional melanocytes may be observed in depigmented skin of some vitiligo patients. The exact cause of the disease is an enigma as the mechanisms underlying melanocyte disappearance are still not known, but several hypotheses have been proposed trying to explain the pathogenesis of vitiligo. The co-occurrence of vitiligo and autoimmune disorders such as thyroid disease, pernicious anaemia, Addison's disease, alopecia areata, systemic lupus erythromatosus, and inflammatory bowel disease, has lead researchers to suspect autoimmune patho-mechanisms. Further evidence for autoimmune aetiology comes from the presence of serum autoantibodies against melanocyte antigens such as the tyrosinase family of enzymes, melanoma antigen recognized by T cells 1 (MART-1), premelanosome protein (PMEL17) and melanocortin-1 receptor in some subjects.

The discovery of melanocyte-specific T cell infiltrates in the advancing margins of lesions and in the peripheral blood compartment along with the ability of these T cells to express the required cytotoxic molecules in the vicinity of melanocytes to cause their destruction has given further credence to the theory that an autoimmune response is central to the pathogenesis of vitiligo.

Several studies have now shown these effector CD8+ T cells to be associated with substantial melanocyte loss in depigmented lesions. The dysfunction of T regulatory cells in the peripheral compartment may be another one of the possible reasons why this aberrant immune response is not controlled. Further, recent studies have shown significant association of HLA alleles and haplotypes. The current treatment regime for vitiligo is thus, focussed on ameliorating the excessive immune activity. These intervention strategies include usage of corticosteroids, calcineurin inhibitors, PUVA (Psoralen plus UVA) and UVB therapy.

Calreticulin (CRT) is a ubiquitous Endoplasmic Reticulum resident calcium-binding protein that primarily functions as a chaperone. Cell surface CRT (Ecto CRT) presentation is proposed to trigger a series of events that lead to activation of effector CD8+ T cells, resulting in immunogeniuc cell death (ICD). This activation pathway is defined during treatment-elicited immunogenic cell death of cancers, where conventional anticancer chemotherapies and radiotherapies activate dendritic cells via CRT pathway, triggering effector T cells. In vitiligo, melanocytes disappear from the lesional skin. Substantial number of melanocyte cell death occurs through CD8+ effector T cells. ICD of melanocytes could be the potential mechanism leading to the activation of CD8+ effector T cells, resulting in melanocyte loss in vitiligo. A recent study has reported a positive relationship between soluble CRT expression in blood plasma and the duration of disease and lesion area in vitiligo patients. CRT overexpression was correlated with the degree of destruction of melanocytes, suggesting that CRT could be a regulator of oxidative stressinduced apoptosis in melanocytes (Y Zhang et al, *Journal of Investigative Dermatology*, 2014).

U.S. Pat. No. 8,927,736 disclosed a method for preparing a 1,2,3-triazole compound comprising contacting an organic azide with a 2-substituted-1-haloalkyne, in the presence of a copper catalyst and a copper-coordinating ligand (preferably a tertiary amine) in a liquid reaction medium, thereby forming a 1,4,5-substituted-1,2,3-triazole compound including a halo substituent at the 5-position of the triazole, the organic portion of the organic azide at the 1-position of the triazole, and the substituent of the 1-iodoalkyne at the 4-position of the triazole.

Article titled "Synthesis of 1H-1,2,3-triazole derivatives by the cyclization of aryl azides with 2-benzothiazolylacetonone, 1,3-benzo-thiazol-2-ylacetonitrile, and (4-aryl-1,3-thiazol-2-yl)acetonitriles" by N T Pokhodylo et al. published in *Chemistry of Heterocyclic Compounds*, 2009, Volume 45, Issue 4, pp 483-488 reports cyclization of aryl azides with 2-benzothiazolylacetone, 1,3-benzothiazol-2-ylacetonitrile, and (4-aryl-1,3-thiazol-2-yl)acetonitriles in methanol in the presence of sodium methylate gives high yields of new products, 2-(5-methyl(amino)-1-aryl-1H-1,2,3-triazol-4-yl)-1,3-benzothiazoles and 1-aryl-(4-aryl-1,3-thiazol-2-yl)-1H-1,2,3-triazole-5-amines.

Article titled "Synthesis of 2-Azido-1,3-thiazoles as 1,2,3-Triazole Precursors" by N T Pokhodylo et al. published in *Synthetic Communications*, 2010, Volume 40, Issue 3, pp 391-399 reports diazotization of 2-aminothiazoles and reaction with sodium azide, the derivatives of 2-azidothiazole. 2-Azidothiazole derivatives were studied in the base-catalysed condensation reactions with activated methylenic compounds to yield new 1-(1,3-thiazol-2-yl)-1H-1,2,3-triazole-4-carboxylic acids.

Vitiligo is considered to be due to autoimmune destruction of melanocytes. The methods and the drugs available in the market for treatment of vitiligo are targeted to suppress immune activity in subjects. However, these treatments do not target the mechanisms that sustain autoimmune reactions, and hence provide only temporary and symptomatic relief.

Therefore, there is need to design synthetic compounds that can suppress the immunogenic cell death (ICD) pathway and exposure of surface calreticulin in melanocytes which can provide new treatment options for stalling vitiligo spread which the prior art has failed to attain. Accordingly, the present inventors propose 1,2,3 triazole-thiazole compounds that can stall or prevent the spread of depigmentation in Vitiligo by suppressing immunogenic cell death of melanocytes and preventing localization of calreticulin to the cell surface of melanocytes.

OBJECTIVE OF INVENTION

The main objective of the present invention is to provide a novel 1,2,3 triazole-thiazole compound of formula (I) or pharmaceutically acceptable salt thereof.

Another objective of the present invention is to provide a process for preparation of novel 1,2,3 triazole-thiazole compound of formula (I).

Yet another objective of the present invention is to provide a pharmaceutical composition comprising compound of formula (I) or pharmaceutically acceptable salt thereof and at least one pharmaceutically acceptable carrier.

Still another objective of the present invention is to provide a method for treating and/or preventing spread of depigmentation in Vitiligo by suppressing immunogenic cell death of melanocytes and preventing localization of calreticulin to the cell surface of melanocytes, wherein said method comprises administering to the subject a therapeutically effective amount of compound of formula (I) or pharmaceutically acceptable salt thereof.

SUMMARY OF THE INVENTION

Accordingly, the present invention provides a novel 1,2,3 triazole-thiazole compound of formula (I);

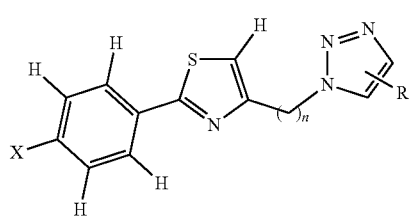

wherein;
R is independently selected from alkyl, cycloalkyl, aryl, aralkyl, hydroxyalkyl or alkoxyalkyl;
n is 1, 2 or 3;
X is a halogen;
or pharmaceutically acceptable salt thereof.

In preferred embodiment, said compound of formula (I) is selected from 2-(4-Chlorophenyl)-4-((4-phenyl-1H-1,2,3-triazol-1-yl)methyl)thiazole (NDS-100971), 2-(4-Chlorophenyl)-4-((4-cyclopropyl-1H-1,2,3-triazol-1-yl)methyl)thiazole (NDS-100972), 4-((4-Butyl-1H-1,2,3-triazol-1-yl)methyl)-2-(4-chlorophenyl)thiazole (NDS-100973), 2-(4-Bromophenyl)-4-((4-butyl-1H-1,2,3-triazol-1-yl)methyl)thiazole, 2-(4-Fluorophenyl)-4-((4-phenyl-1H-1,2,3-triazol-1-yl)methyl)thiazole 4-((4-Benzyl-1H-1,2,3-triazol-1-yl)methyl)-2-(4-fluorophenyl)thiazole, 4-((4-Cyclohexyl-1H-1,2,3-triazol-1-yl)methyl)-2-(4-fluorophenyl)thiazole, 4-((4-Cyclopropyl-1H-1,2,3-triazol-1-yl)methyl)-2-(4-fluorophenyl)thiazole, 2-(4-Fluorophenyl)-4-((4-propyl-1H-1,2,3-triazol-1-yl)methyl) thiazole, 2-(4-Bromophenyl)-4-((4-propyl-1H-1,2,3-triazol-1-yl)methyl)thiazole, 2-(4-Chlorophenyl)-4-((4-propyl-1H-1,2,3-triazol-1-yl)methyl)thiazole, 4-((4-Benzyl-1H-1,2,3-triazol-1-yl)methyl)-2-(4-chlorophenyl)thiazole, 2-(4-Bromophenyl)-4-((4-cyclohexyl-1H-1,2,3-triazol-1-yl)methyl)thiazole, 2-(4-Chlorophenyl)-4-((4-cyclohexyl-1H-1,2,3-triazol-1-yl)methyl)thiazole, 2-(4-Bromo phenyl)-4-((4-cyclopentyl-1H-1,2,3-triazol-1-yl) methyl)thiazole, 2-(4-Chloro phenyl)-4-((4-cyclopentyl-1H-1,2,3-triazol-1-yl) methyl) thiazole, 4-((4-Cyclopentyl-1H-1,2,3-triazol-1-yl)methyl)-2-(4-fluorophenyl)thiazole, (1-((2-(4-Fluorophenyl)thiazol-4-yl)methyl)-1H-1,2,3-triazol-4-yl)methanol, (1-((2-(4-Chlorophenyl)thiazol-4-yl)methyl)-1H-1,2,3-triazol-4-yl) methanol, (1-((2-(4-Bromophenyl)thiazol-4-yl)methyl)-1H-1,2,3-triazol-4-yl)methanol, 2-(4-Bromophenyl)-4-((4-(methoxymethyl)-1H-1,2,3-triazol-1-yl)methyl) thiazole, 2-(4-Chlorophenyl)-4-((4-(methoxymethyl)-1H-1,2,3-triazol-1-yl)methyl) thiazole, 2-(4-Fluorophenyl)-4-((4-(methoxymethyl)-1H-1,2,3-triazol-1-yl)methyl) thiazole, 2-(4-Fluorophenyl)-4-((4-(p-tolyl)-1H-1,2,3-triazol-1-yl) methyl)thiazole, 2-(4-Bromophenyl)-4-((4-(p-tolyl)-1H-1,2,3-triazol-1-yl)methyl) thiazole, 2-(4-Chlorophenyl)-4-((4-(p-tolyl)-1H-1,2,3-triazol-1-yl)methyl)thiazole, 2-(4-Chlorophenyl)-4-(2-(4-phenyl-1H-1,2,3-triazol-1-yl)ethyl) thiazole, 2-(4-Bromophenyl)-4-(2-(4-phenyl-1H-1,2,3-triazol-1-yl)ethyl)thiazole, 2-(4-Fluorophenyl)-4-(2-(4-phenyl-1H-1,2,3-triazol-1-yl)ethyl)thiazole, 2-(4-Chlorophenyl)-4-(2-(4-cyclopropyl-1H-1,2,3-triazol-1-yl) ethyl)thiazole, 2-(4-Bromophenyl)-4-(2-(4-cyclopropyl-1H-1,2,3-triazol-1-yl)ethyl)thiazole, 4-(2-(4-Cyclopropyl-1H-1,2,3-triazol-1-yl)ethyl)-2-(4-fluorophenyl) thiazole, (1-(2-(2-(4-Fluorophenyl)thiazol-4-yl)ethyl)-1H-1,2,3-triazol-4-yl) methanol, (1-(2-(2-(4-Bromophenyl)thiazol-4-yl)ethyl)-1H-1,2,3-triazol-4-yl)methanol, (1-(2-(2-(4-Chlorophenyl)thiazol-4-yl)ethyl)-1H-1,2,3-triazol-4-yl)methanol, 2-(4-Fluorophenyl)-4-(2-(4-(methoxymethyl)-1H-1,2,3-triazol-1-yl)ethyl)thiazole, 2-(4-Chlorophenyl)-4-(2-(4-(methoxymethyl)-1H-1,2,3-triazol-1-yl)ethyl)thiazole, 2-(4-Bromophenyl)-4-(2-(4-(methoxymethyl)-1H-1,2,3-triazol-1-yl)ethyl)thiazole, 2-(4-Bromophenyl)-4-(2-(5-(p-tolyl)-1H-1,2,3-triazol-1-yl)ethyl)thiazole, 2-(4-Fluorophenyl)-4-(2-(5-phenyl-1H-1,2,3-triazol-1-yl)ethyl)thiazole, 2-(4-Chlorophenyl)-4-(2-(5-phenyl-1H-1,2,3-triazol-1-yl)ethyl) thiazole, 2-(4-Bromophenyl)-4-(2-(5-phenyl-1H-1,2,3-triazol-1-yl)ethyl)thiazole, 2-(4-Bromophenyl)-4-(2-(5-propyl-1H-1,2,3-triazol-1-yl)ethyl)thiazole, 2-(4-Fluorophenyl)-4-(2-(5-propyl-1H-1,2,3-triazol-1-yl)ethyl) thiazole, 2-(4-Chlorophenyl)-4-(2-(5-propyl-1H-1,2,3-triazol-1-yl)ethyl)thiazole, 4-(2-(5-Cyclopropyl-1H-1,2,3-triazol-1-yl)ethyl)-2-(4-fluorophenyl)thiazole, 2-(4-Chlorophenyl)-4-(2-(5-cyclopropyl-1H-1,2,3-triazol-1-yl) ethyl)thiazole, 2-(4-Bromophenyl)-4-(2-(5-cyclopropyl-1H-1,2,3-triazol-1-yl)ethyl)thiazole, (1-(2-(2-(4-Fluorophenyl) thiazol-4-yl)ethyl)-1H-1,2,3-triazol-5-yl) methanol, (1-(2-(2-(4-Chlorophenyl)thiazol-4-yl)ethyl)-1H-1,2,3-triazol-5-yl) methanol, (1-(2-(2-(4-Bromophenyl)thiazol-4-yl)ethyl)-1H-1,2,3-triazol-5-yl)methanol.

In an embodiment, the present invention provides a process for the preparation of 1,2,3 triazole-thiazole compound of formula (I) comprising the steps of:
a) adding sodium azide to a solution of chloro compound in solvent followed by stirring the reaction mixture at temperature in the range of 50 to 60° C. for the period in the range of 5 to 6 hours to afford corresponding azido compound;
b) adding the azido compound of step (a) to a solution of copper (II) sulfate pentahydrate, reducing agent and alkyne in suitable solvent followed by stirring the reaction mixture at temperature in the range of 25 to 32° C. for the period in the range of 5 to 6 hours.

In preferred embodiment, said chloro compound is selected from 4-(chloromethyl)-2-(4-chlorophenyl)thiazole, 4-(chloromethyl)-2-(4-bromophenyl)thiazole, 4-(chloromethyl)-2-(4-Fluorophenyl)thiazole or 4-(chloromethyl)-2-(4-iodophenyl)thiazole.

In another preferred embodiment, said azido compound is selected from 4-(Azidomethyl)-2-(4-chlorophenyl)thiazole, 4-(azidomethyl)-2-(4-bromophenyl)thiazole, 4-(azidomethyl)-2-(4-fluorophenyl)thiazole or 4-(azidomethyl)-2-(4-iodophenyl)thiazole.

In yet another preferred embodiment, said solvent is selected from polar aprotic solvent such as DMF or DMPU, t-butanol, water or mixture thereof.

In still another preferred embodiment, said additive is selected from sodium ascorbate, 2-ethynylpyridine or triethyl amine.

In yet still another preferred embodiment, said alkyne is R—C≡CH wherein 'R' is independently selected from alkyl, cycloalkyl, aryl, aralkyl, hydroxyalky or alkoxyalkyl.

In yet still another preferred embodiment, said alkyne is selected from phenyl acetylene. cyclopropylacetylene, 1-hexyne, 1-heptyne, 5-hexyn-1-ol or ethylpropiolate.

In another embodiment, the present invention provides a pharmaceutical composition comprising novel 1,2,3 triazole-thiazole compound of formula (I) or pharmaceutically acceptable salt thereof and at least one pharmaceutically acceptable carrier.

In yet another embodiment, the present invention provides a method for treating and/or preventing spread of depigmentation in Vitiligo by suppressing immunogenic cell death of melanocytes and preventing localization of calreticulin to the cell surface of melanocytes, wherein said method comprises administering to the subject a therapeutically effective amount of compound of formula (I) or pharmaceutically acceptable salt thereof.

In preferred embodiment, said subject is human.

BRIEF DESCRIPTION OF THE DRAWINGS

FIG. 1: B16 cells were left untreated or treated with different concentrations of compounds of Formula I added to the culture media (DMEM+10% FBS). After 6 hours of incubation at 37° C., 5% $CO_2$, Cisplatin was added to the same culture media at a final concentration of 100 µg/mL. Incubations were carried out at 37° C., 5% $CO_2$ for 18 hours. Surface calreticulin was stained with antibody and quantitated by Imaging FACS. The data is represented as percentage of total cells that are CRT positive. Detailed protocol is mentioned in the experimental details section below.

DETAILED DESCRIPTION OF THE INVENTION

The invention will now be described in detail in connection with certain preferred and optional embodiments, so that various aspects thereof may be more fully understood and appreciated.

In view of above, the present invention provides a novel 1,2,3 triazole-thiazole compound of formula (I) that can stall or prevent the spread of depigmentation in Vitiligo by suppressing immunogenic cell death of melanocytes and preventing localization of calreticulin to the cell surface of melanocytes.

In an embodiment, the present invention relates to novel 1,2,3 triazol-thiazole compound of formula (I) or its acid addition salts or isomers or analogues or enantiomers thereof;

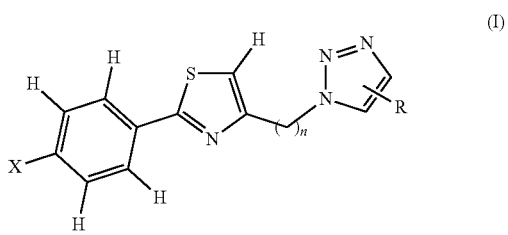

wherein,
'R' is independently selected from alkyl, cycloalkyl, aryl, aralkyl, hydroxyalky or alkoxyalkyl;
'n' is 1, 2 or 3;
'X' is halogen.

In preferred embodiment, the compound of formula (I) is selected from 2-(4-Chlorophenyl)-4-((4-phenyl-1H-1,2,3-triazol-1-yl)methyl)thiazole (NDS-100971), 2-(4-Chlorophenyl)-4-((4-cyclopropyl-1H-1,2,3-triazol-1-yl)methyl)thiazole (NDS-100972), 4-((4-Butyl-1H-1,2,3-triazol-1-yl)methyl)-2-(4-chlorophenyl)thiazole (NDS-100973), 2-(4-Bromophenyl)-4-((4-butyl-1H-1,2,3-triazol-1-yl)methyl)thiazole, 2-(4-Fluorophenyl)-4-((4-phenyl-1H-1,2,3-triazol-1-yl)methyl)thiazole 4-((4-Benzyl-1H-1,2,3-triazol-1-yl)methyl)-2-(4-fluorophenyl)thiazole, 4-((4-Cyclohexyl-1H-1,2,3-triazol-1-yl)methyl)-2-(4-fluorophenyl)thiazole, 4-((4-Cyclopropyl-1H-1,2,3-triazol-1-yl)methyl)-2-(4-fluorophenyl)thiazole, 2-(4-Fluorophenyl)-4-((4-propyl-1H-1,2,3-triazol-1-yl)methyl) thiazole, 2-(4-Bromophenyl)-4-((4-propyl-1H-1,2,3-triazol-1-yl)methyl)thiazole, 2-(4-Chlorophenyl)-4-((4-propyl-1H-1,2,3-triazol-1-yl)methyl) thiazole, 4-((4-Benz yl-1H-1,2,3-triazol-1-yl)methyl)-2-(4-chlorophenyl)thiazole, 2-(4-Bromophenyl)-4-((4-cyclohexyl-1H-1,2,3-triazol-1-yl)methyl)thiazole, 2-(4-Chlorophenyl)-4-((4-cyclohexyl-1H-1,2,3-triazol-1-yl) methyl)thiazole, 2-(4-Bromo phenyl)-4-((4-cyclopentyl-1H-1,2,3-triazol-1-yl) methyl)thiazole, 2-(4-Chloro phenyl)-4-((4-cyclopentyl-1H-1,2,3-triazol-1-yl) methyl) thiazole, 4-((4-Cyclopentyl-1H-1,2,3-triazol-1-yl)methyl)-2-(4-fluorophenyl)thiazole, (1-((2-(4-Fluorophenyl)thiazol-4-yl)methyl)-1H-1,2,3-triazol-4-yl)methanol, (1-((2-(4-Chlorophenyl)thiazol-4-yl)methyl)-1H-1,2,3-triazol-4-yl) methanol, (1-((2-(4-Bromophenyl)thiazol-4-yl)methyl)-1H-1,2,3-triazol-4-yl)methanol, 2-(4-Bromophenyl)-4-((4-(methoxymethyl)-1H-1,2,3-triazol-1-yl)methyl) thiazole, 2-(4-Chlorophenyl)-4-((4-(methoxymethyl)-1H-1,2,3-triazol-1-yl)methyl) thiazole, 2-(4-Fluorophenyl)-4-((4-(methoxymethyl)-1H-1,2,3-triazol-1-yl)methyl) thiazole, 2-(4-Fluorophenyl)-4-((4-(p-tolyl)-1H-1,2,3-triazol-1-yl)methyl)thiazole, 2-(4-Bromophenyl)-4-((4-(p-tolyl)-1H-1,2,3-triazol-1-yl)methyl) thiazole, 2-(4-Chlorophenyl)-4-((4-(p-tolyl)-1H-1,2,3-triazol-1-yl)methyl)thiazole, 2-(4-Chlorophenyl)-4-(2-(4-phenyl-1H-1,2,3-triazol-1-yl)ethyl) thiazole, 2-(4-Bromophenyl)-4-(2-(4-phenyl-1H-1,2,3-triazol-1-yl)ethyl)thiazole, 2-(4-Fluorophenyl)-4-(2-(4-phenyl-1H-1,2,3-triazol-1-yl)ethyl)thiazole, 2-(4-Chlorophenyl)-4-(2-(4-cyclopropyl-1H-1,2,3-triazol-1-yl) ethyl)thiazole, 2-(4-Bromophenyl)-4-(2-(4-cyclopropyl-1H-1,2,3-triazol-1-yl)ethyl)thiazole, 4-(2-(4-Cyclopropyl-1H-1,2,3-triazol-1-yl)ethyl)-2-(4-fluorophenyl) thiazole, (1-(2-(2-(4-Fluorophenyl)thiazol-4-yl)ethyl)-1H-1,2,3-triazol-4-yl)methanol, (1-(2-(2-(4-Bromophenyl)thiazol-4-yl)ethyl)-1H-1,2,3-triazol-4-yl)methanol, (1-(2-(2-(4-Chlorophenyl)thiazol-4-yl)ethyl)-1H-1,2,3-triazol-4-yl)methanol, 2-(4-Fluorophenyl)-4-(2-(4-(methoxymethyl)-1H-1,2,3-triazol-1-yl)ethyl)thiazole, 2-(4-Chlorophenyl)-4-(2-(4-

(methoxymethyl)-1H-1,2,3-triazol-1-yl)ethyl)thiazole, 2-(4-Bromophenyl)-4-(2-(4-(methoxymethyl)-1H-1,2,3-triazol-1-yl)ethyl)thiazole, 2-(4-Bromophenyl)-4-(2-(5-(p-tolyl)-1H-1,2,3-triazol-1-yl)ethyl)thiazole, 2-(4-Fluorophenyl)-4-(2-(5-phenyl-1H-1,2,3-triazol-1-yl)ethyl)thiazole, 2-(4-Chlorophenyl)-4-(2-(5-phenyl-1H-1,2,3-triazol-1-yl)ethyl)thiazole, 2-(4-Bromophenyl)-4-(2-(5-phenyl-1H-1,2,3-triazol-1-yl)ethyl)thiazole, 2-(4-Bromophenyl)-4-(2-(5-propyl-1H-1,2,3-triazol-1-yl)ethyl)thiazole, 2-(4-Fluorophenyl)-4-(2-(5-propyl-1H-1,2,3-triazol-1-yl)ethyl)thiazole, 2-(4-Chlorophenyl)-4-(2-(5-propyl-1H-1,2,3-triazol-1-yl)ethyl)thiazole, 4-(2-(5-Cyclopropyl-1H-1,2,3-triazol-1-yl)ethyl)-2-(4-fluorophenyl)thiazole, 2-(4-Chlorophenyl)-4-(2-(5-cyclopropyl-1H-1,2,3-triazol-1-yl)ethyl)thiazole, 2-(4-Bromophenyl)-4-(2-(5-cyclopropyl-1H-1,2,3-triazol-1-yl)ethyl)thiazole, (1-(2-(2-(4-Fluorophenyl)thiazol-4-yl)ethyl)-1H-1,2,3-triazol-5-yl) methanol, (1-(2-(2-(4-Chlorophenyl)thiazol-4-yl)ethyl)-1H-1,2,3-triazol-5-yl) methanol, (1-(2-(2-(4-Bromophenyl)thiazol-4-yl)ethyl)-1H-1,2,3-triazol-5-yl)methanol.

In another embodiment, the present invention provides a process for the preparation of 1,2,3 triazole-thiazole compound of formula (I) comprising the steps of:
a) adding sodium azide to a solution of chloro compound in solvent followed by stirring the reaction mixture at temperature in the range of 50 to 60° C. for the period in the range of 5 to 6 hours to afford corresponding azido compound;
b) adding the azido compound of step (a) to a solution of copper (II) Sulfate Pentahydrate, reducing agent and alkyne in suitable solvent followed by stirring the reaction mixture at temperature in the range of 25 to 32° C. for the period in the range of 5 to 6 hours.

In preferred embodiment, said chloro compound is selected from 4-(chloromethyl)-2-(4-chlorophenyl)thiazole, 4-(chloromethyl)-2-(4-bromophenyl)thiazole, 4-(chloromethyl)-2-(4-Fluorophenyl)thiazole or 4-(chloromethyl)-2-(4-iodophenyl)thiazole.

In another preferred embodiment, said azido compound is selected from 4-(Azidomethyl)-2-(4-chlorophenyl)thiazole, 4-(azidomethyl)-2-(4-bromophenyl)thiazole, 4-(azidomethyl)-2-(4-fluorophenyl)thiazole or 4-(azidomethyl)-2-(4-iodophenyl)thiazole. In yet another preferred embodiment, said solvent is selected from polar aprotic solvent such as DMF or DMPU, t-butanol, water or mixture thereof.

In still another preferred embodiment, said additive is selected from sodium ascorbate, 2-ethynylpyridine or triethyl amine.

In yet still another preferred embodiment, said alkyne is R—C≡CH wherein 'R' is independently selected from alkyl, cycloalkyl, aryl, aralkyl, hydroxyalky or alkoxyalkyl.

In yet still another preferred embodiment, said alkyne is selected from phenyl acetylene. cyclopropylacetylene, 1-hexyne, 1-heptyne, 5-hexyn-1-ol or ethylpropiolate.

The solvents are selected from polar protic solvents such as water, $C_1$ to $C_5$ alcohols such as methanol, ethanol, isopropanol, n-butanol, t-butanol and the like; acids such as formic acid or acetic acid; or polar aprotic solvents such as dimethylformamide (DMF), tetrahydrofuran (THF), 3-Dimethyl-3,4,5,6-tetrahydro-2(1H)-pyrimidinone (DMPU) or 1,3-Dimethyl-2-imidazolidinone (DMI); either alone or in mixtures thereof. Preferably, the solvents for step (b) is selected from polar aprotic solvent such as DMF or DMPU. The solvent for step (c) is preferably a mixture of t-butanol and water.

The cycloaddition is catalyzed using active Cu(I) catalyst that can be generated from Cu(I) salts or Cu(II) salts using sodium ascorbate as the reducing agent. Preferably, the copper salt is Cu(II) salt such as $CuSO_4$, $CuBr_2$, $CuCO_3$ and the like.

The process is shown in Scheme 1 below:

Scheme 1:

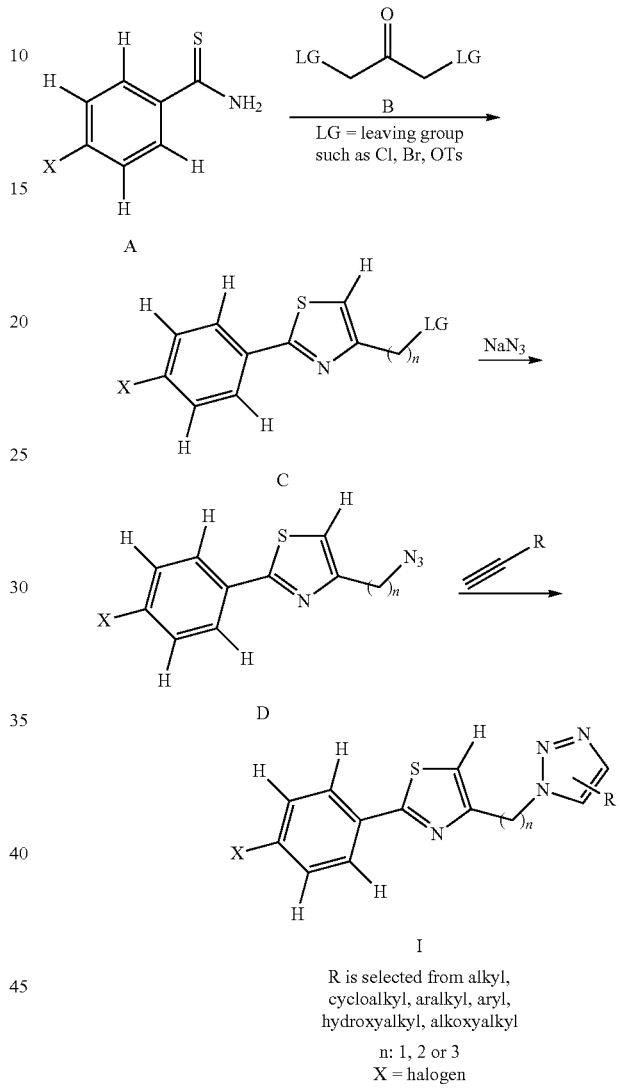

R is selected from alkyl, cycloalkyl, aralkyl, aryl, hydroxyalkyl, alkoxyalkyl n: 1, 2 or 3
X = halogen The process for the preparation of compounds 1 to 9 is depicted in Scheme 2 below:

Scheme 2:

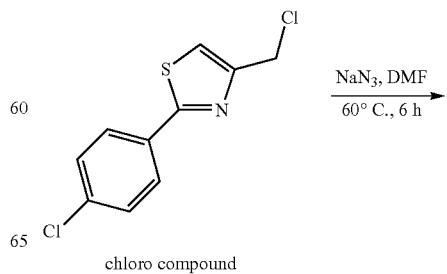

chloro compound

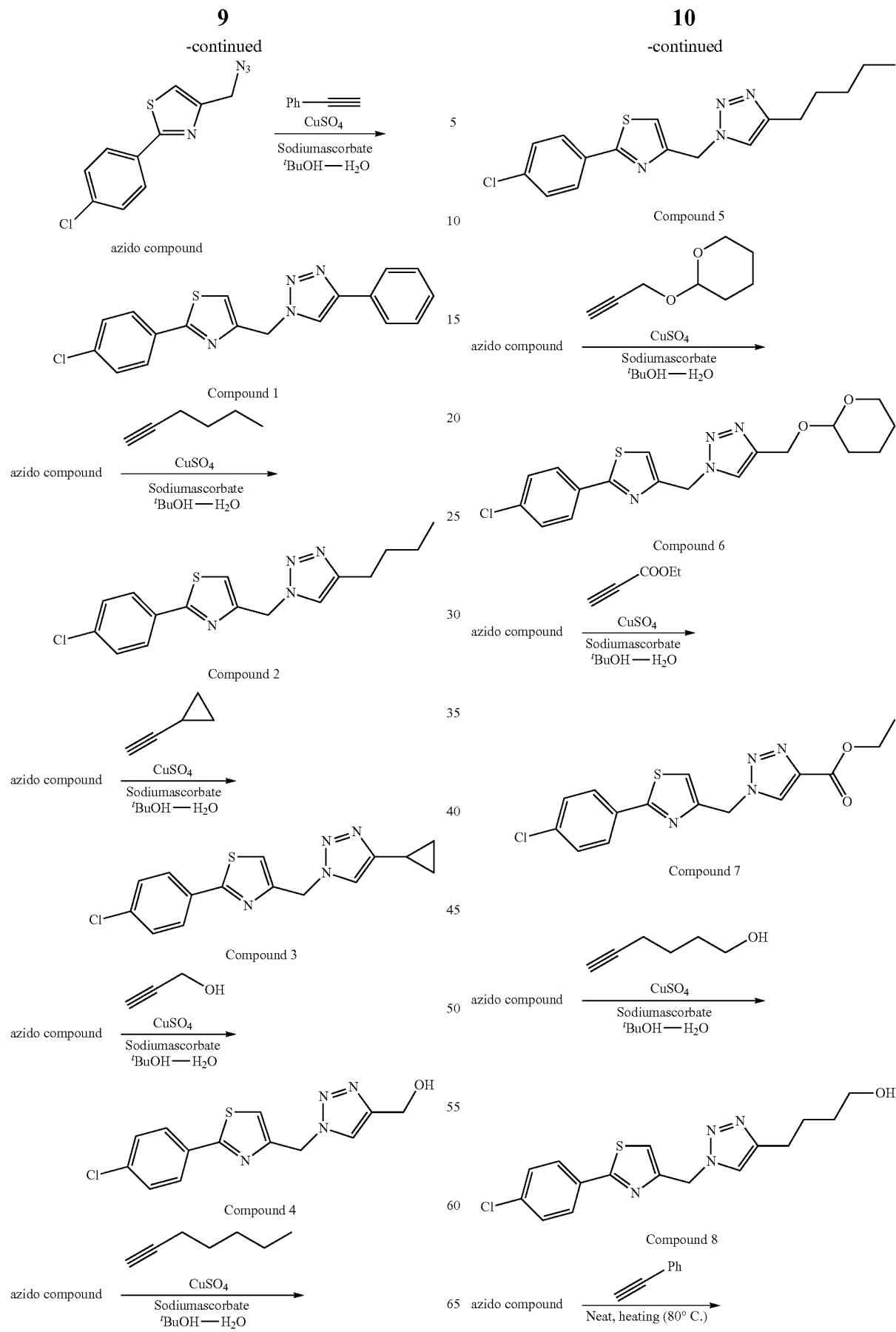

-continued

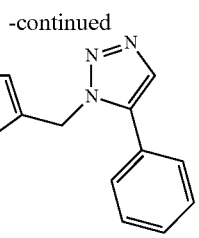

Compound 9

+ Compound 1

In yet another embodiment, the present invention provides a pharmaceutical composition comprising 1,2,3 triazol-thiazole compound of formula (I) or its acid addition salts or isomers or analogues or enantiomers either alone or as mixtures thereof as active ingredient and at least one pharmaceutically acceptable carrier, diluent or excipient.

The pharmaceutical composition comprising compounds of formula (I) suppresses the immunogenic cell death (ICD) pathway and exposure of surface calreticulin in melanocytes and thus provide novel treatment for stalling vitiligo spread and/or provide prophylactic treatment option for individuals with vitiligo predisposition.

The pharmaceutical composition according to the invention can be in the form of a solid, for example, powders, granules, tablets, capsules or can be present in the liquid form such as solutions, emulsions, suspensions etc or topical or as an injectable composition.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres.

In another embodiment, the present invention relates to administering 'an effective amount' of the 'composition of invention' to the subject suffering from said disease. Therapeutically or prophylactically effective amount used herein refers to dose or amount of drug that produces a therapeutic response or desired effect in the subjects when administered. Accordingly, compound of formula (I) and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

The pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

In yet another embodiment, the present invention provides a method for treating and/or preventing spread of depigmentation in Vitiligo by suppressing immunogenic cell death of melanocytes and preventing localization of calreticulin to the cell surface of melanocytes, wherein said method comprises administering to the subject a therapeutically effective amount of compound of formula (I) or pharmaceutically acceptable salt thereof.

In preferred embodiment, said subject is human.

In another preferred embodiment, the present invention provides a method for suppressing immunogenic cell death (ICD) and exposure of surface calreticulin in melanocytes thereby treating or preventing the vitiligo spread comprising administering to a subject in need, the pharmaceutical composition of compounds of formula (I) or its acid addition salts or analogues or stereoisomers either alone or in combination as active ingredient in therapeutically effective amount.

In yet another embodiment, the present invention relates to the use of compounds of formula (I) or its acid addition salts or analogues or stereoisomers thereof for suppressing immunogenic cell death (ICD) and exposure of surface calreticulin in melanocytes thereby treating or preventing the vitiligo spread in a subject or provide prophylactic treatment option for individuals with vitiligo predisposition.

From FIG. 1 it is observed that the compounds of the NDS series are able to suppress Cisplatin-mediated translocation of Calreticulin on the surface of the B16 cells (as observed by staining with calreticulin antibody) in the concentration range of 50-125 µM.

Further details of the present invention will be apparent from the examples presented below. Examples presented are purely illustrative and are not limited to the particular embodiments illustrated herein but include the permutations, which are obvious as set forth in the description.

EXAMPLES

Example 1: Preparation of 4-(Azidomethyl)-2-(4-chlorophenyl)thiazole

NaN$_3$ (400 mg, 6.15 mmol) was added to a solution of chloro compound (1.0 g, 4.1 mmol) in DMF (10 mL) and stirred at 60° C. for 6 h. The reaction mass was quenched with water (20 mL) and extracted with diethyl ether (3×10 mL). The combined organic layers were washed with brine (20 mL), dried over anhydrous Na$_2$SO$_4$ evaporated under reduced pressure. The crude reaction mass was purified by silica gel column chromatography using (30%) EtOAc in petroleum ether to afford azido compound (520 mg, 54%) as light yellow liquid.

Example 2: Preparation of 2-(4-Chlorophenyl)-4-((4-phenyl-1H-1,2,3-triazol-1-yl)methyl)thiazole (compound 1; NDS-100971)

Azido compound 4-(azidomethyl)-2-(4-chlorophenyl)thiazole (120 mg, 0.48 mmol) was added to a solution of CuSO$_4$.5H$_2$O (24 mg, 0.2 mmol), sodium ascorbate (91 mg, 0.46 mmol), phenyl acetylene (50 µL, 0.43 mmol) in 3:1 $^t$BuOH-water (5.0 mL) and stirred at room temperature 25-30° C. for 6 h. The reaction mass was diluted with water (10 mL), extracted with EtOAc (3×10 mL), combined organic layers were washed with brine (10 mL) dried over anhydrous Na$_2$SO$_4$ evaporated under reduced pressure, crude reaction mass was purified by silica gel (230-400 mesh) column chromatography using (30%) EtOAc in petroleum ether to afford compound 1 (80 mg, 48%) as off-white solid. IR$\upsilon_{max}$(film): 3386, 3085, 2288, 1644, 1501, 1448, 1275 cm$^{-1}$; $^1$H NMR (CDCl$_3$, 400 MHz) δ 7.98 (s, 1H), 7.91-7.78 (m, 4H), 7.49-7.24 (m, 5H), 7.24 (s, 1H), 5.73 (s, 2H); $^{13}$C NMR (CDCl$_3$, 100 MHz) δ 168.0, 150.8, 148.1, 136.5, 131.5, 130.5, 129.2, 128.8, 128.2, 127.7, 125.7, 120.0, 117.8, 49.9; LC-MS: (M+H) 353.0; M.P: 145-146° C.

Example 3: Preparation of 4-((4-Butyl-1H-1,2,3-triazol-1-yl)methyl)-2-(4-chlorophenyl)thiazole (Compound 2: NDS-100973)

Compound 2 was prepared using the similar procedure employed in the preparation of compound 1.

Yield=47%, M.P: 98-99° C.; IR$\upsilon_{max}$(film): 3574, 2923, 1646, 1601, 1452, 1222 cm$^{-1}$; $^1$H NMR (CDCl$_3$, 400 MHz) δ 7.96-7.71 (m, 2H), 7.48 (s, 1H), 7.45-7.32 (m, 2H), 7.15 (s, 1H), 5.64 (s, 2H), 2.71 (t, J=7.8 Hz, 2H), 1.74-1.55 (m, 2H), 1.44-1.29 (m, 2H), 0.91 (t, J=7.3 Hz, 3H); $^{13}$C NMR (CDCl$_3$, 100 MHz) δ 167.8, 151.2, 148.8, 136.4, 131.6, 129.2, 127.7, 121.0, 117.5, 49.7, 31.5, 25.3, 22.3, 13.8; LC-MS: (M+H) 333.1.

Example 4: Preparation of 2-(4-Chlorophenyl)-4-((4-cyclopropyl-1H-1,2,3-triazol-1-yl)methyl)thiazole (Compound 3: NDS-100972)

Compound 3 was prepared using the similar procedure employed in the preparation of compound 1.

Yield=52%, M.P: 109-111° C.; IR$\upsilon_{max}$(film): 3016, 2960, 1640, 1507, 1455, 1340, 1217 cm$^{-1}$; $^1$H NMR (CDCl$_3$, 400 MHz) δ 7.96-7.71 (m, 2H), 7.52-7.33 (m, 3H), 7.16 (s, 1H), 5.62 (s, 2H), 2.00-1.89 (m, 1H), 0.98-0.88 (m, 2H), 0.87-0.77 (m, 2H); $^{13}$C NMR (CDCl$_3$, 100 MHz) δ 167.8, 151.1, 150.6, 136.4, 131.6, 129.2, 127.7, 120.1, 117.6, 49.7, 7.7, 6.7; LC-MS: (M+H) 317.1.

Example 5: Preparation of (1-((2-(4-Chlorophenyl)thiazol-4-yl)methyl)-1H-1,2,3-triazol-4-yl)methanol (Compound 4: NDS-101210)

Compound 4 was prepared using the similar procedure employed in the preparation of compound 1.

M.P: 152-154° C.; $^1$H NMR (DMSO-d$_6$, 400 MHz) δ 8.05 (s, 1H), 7.92 (d, J=7.9 Hz, 2H), 7.73 (s, 1H), 7.55 (d, J=7.9 Hz, 2H), 5.73 (s, 2H), 5.18 (br. s., 1H), 4.52 (s, 2H); $^{13}$C NMP (DMSO-d$_6$, 100 MHz) δ 166.5, 151.5, 148.3, 135.0, 131.5, 129.3, 127.8, 123.0, 119.4, 55.0, 48.8. MS (M+H): 307.

Example 6: Preparation of 2-(4-Chlorophenyl)-4-((4-pentyl-1H-1,2,3-triazol-1-yl)methyl)thiazole: (Compound 5: NDS 101211)

Compound 5 was prepared using the similar procedure employed in the preparation of compound 1.

M.P: 88-90° C.; $^1$H NMR (CDCl$_3$, 400 MHz) δ 7.87 (d, J=8.5 Hz, 2H), 7.50 (s, 1H), 7.43 (d, J=8.5 Hz, 2H), 7.18 (s, 1H), 5.67 (s, 2H), 2.72 (t, J=7.6 Hz, 2H), 1.76-1.46 (m, 2H), 1.34 (d, J=3.7 Hz, 4H), 0.89 (t, J=6.7 Hz, 3H); $^{13}$C NMR (CDCl$_3$, 100 MHz) δ 167.8, 151.2, 148.8, 136.4, 131.6, 129.2, 127.7, 121.0, 117.5, 49.7, 31.4, 29.1, 25.6, 22.4, 14.0. MS (M+H) 347.

Example 7: Preparation of 2-(4-Chlorophenyl)-4-((4-(((tetrahydro-2H-pyran-2-yl)oxy)methyl)-1H-1,2,3-triazol-1-yl)methyl)thiazole: (Compound 6: NDS 101214)

Compound 6 was prepared using the similar procedure employed in the preparation of compound 1.

M.P: 92-94° C.; $^1$H NMR (CDCl$_3$, 400 MHz) δ 7.85 (d, J=8.5 Hz, 2H), 7.79 (s, 1H), 7.41 (d, J=8.5 Hz, 2H), 7.22 (s, 1H), 5.68 (s, 2H), 4.88 (d, J=12.2 Hz, 1H), 4.74 (t, J=3.4 Hz, 1H), 4.65 (d, 1H, 4.01-3.72 (m, 1H), 3.62-3.32 (m, 1H), 1.88-1.67 (m, 2H), 1.67-1.39 (m, 4H); $^{13}$C NMR (CDCl$_3$, 100 MHz) δ 167.8, 150.6, 145.4, 136.4, 131.5, 129.2, 127.7, 123.0, 117.8, 98.2, 62.3, 60.5, 49.7, 30.4, 25.3, 19.3. MS (M+H) 391.

Example 8: Preparation of Ethyl 1-((2-(4-chlorophenyl)thiazol-4-yl)methyl)-1H-1,2,3-triazole-4-carboxylate (Compound 7: NDS 101213)

Compound 7 was prepared using the similar procedure employed in the preparation of compound 1.

M.P: 149-151° C.; $^1$H NMR (DMSO-d$_6$, 400 MHz) δ 8.86 (s, 1H), 7.90 (d, J=7.9 Hz, 2H), 7.77 (s, 1H), 7.54 (d, J=7.9 Hz, 2H), 5.83 (s, 2H), 4.30 (q, J=6.7 Hz, 2H), 1.29 (t, J=6.7 Hz, 3H); $^{13}$C NMR (DMSO-d$_6$, 100 MHz) δ 166.6, 160.1, 150.7, 138.9, 135.0, 131.3, 129.4, 129.3, 127.8, 119.6, 60.5, 49.1, 14.1; MS (M+H) 349.

Example 9: Preparation of 4-(1-((2-(4-Chlorophenyl)thiazol-4-yl)methyl)-1H-1,2,3-triazol-4-yl)butan-1-ol: (Compound 8: NDS 101212)

Compound 8 was prepared using the similar procedure employed in the preparation of compound 1.

M.P: 157-159° C.; $^1$H NMR (CDCl$_3$, 400 MHz) δ 7.86 (d, J=7.9 Hz, 2H), 7.52 (s, 1H), 7.42 (d, J=7.9 Hz, 2H), 7.19 (s, 1H), 5.65 (s, 2H), 3.66 (t, J=6.1 Hz, 2H), 2.75 (t, J=7.3 Hz, 2H), 1.83-1.70 (m, 2H), 1.70-1.41 (m, 2H). $^{13}$C NMR (CDCl$_3$, 100 MHz) δ 167.9, 150.9, 148.3, 136.4, 131.5, 129.2, 127.7, 121.2, 117.7, 62.3, 49.7, 32.0, 25.5, 25.2. MS (M+H) 349;

Example 10: Preparation of 2-(4-chlorophenyl)-4-((5-phenyl-1H-1,2,3-triazol-1-yl)methyl)thiazole: (Compound 9: NDS 101235)

Compound 9 was prepared by reacting a neat mixture of azido compound 4-(azidomethyl)-2-(4-chlorophenyl)thiazole (1.0 equiv) and phenyl acetylene (1.2 equiv) at 80° C. for 16 h, the reaction mixture was then cooled to room temperature and was carefully purified by column chromatography over 230-400 mesh silica gel to afford a compound 9 and compound 1.

Compound 9: M.P: 175-177° C.; $^1$H NMR (CDCl$_3$, 400 MHz) δ 7.83-7.78 (m, 3H), 7.52-7.39 (m, 7H), 7.05 (s, 1H), 5.70 (s, 2H); $^{13}$C NMR (CDCl$_3$, 100 MHz) δ 167.5, 151.8, 138.4, 136.3, 133.0, 131.7, 129.6, 129.2, 129.1, 128.9, 127.7, 126.7, 117.1, 48.1. MS (M+H): 353. Data for the compound 1 is provided hereinabove.

Example 11: Protocol for ECTO-CRT FACS (Plasma Membrane Surface Calreticulin-Fluorescence-Activated Cell Sorting/Flow Cytometry)

1. B16 cells were maintained at 60-80% confluence at 5% CO$_2$ levels in DMEM medium supplemented with 10% Fetal bovine serum (FBS, heat inactivated). The source of B16 cells was ATCC (CRL 6475).

2. For setting up of experiment, 5-10$^5$ cells were plated per T-25 flask under the same conditions as mentioned above and left overnight.

3. The cells were then treated with the selected compounds of Formula (I) (solubilized in DMSO solution, Sigma) at the concentrations mentioned in FIG. 1 and incubation was carried out at 37° C., 5% $CO_2$ for 6 hours.

4. In a subset of flasks, Cisplatin (Sigma, Cat number P43994) was added to a final concentration of 100 μg/ml of media and incubations with B16 cells were carried out at 37° C., 5% $CO_2$ for 18 hours. Cisplatin for addition stock was prepared in DMF (dimethylformamide) solution at a concentration of 15 mg/ml.

5. The experiment was terminated by harvesting B16 cells by trypsinization using 0.1% Trypsin-EDTA solution (Thermo Fisher Scientific). The cells were pelleted by centrifugation at 600 g, 4° C. for 5 minutes.

6. The cell pellet was washed with cold solution of 2% fetal bovine serum (FBS, Life Technologies) in phosphate buffer saline (PBS) containing 0.1% sodium azide (FACS solution).

7. Cells were then incubated with calreticulin antibody (Abcam, catalog number: ab2907) prepared in FACS solution at a final dilution of 1:100 for 1 hour at 4° C.

8. The cells were then washed twice with cold FACS solution and incubated with secondary antibody (Alexa fluor 488 conjugated anti rabbit, Thermo Fischer, Catalog number A-110034) prepared in FACS solution at a final dilution of 1:500 for 40 minutes at 4° C.

9. The cells were then washed twice with cold FACS solution and resuspended in cold PBS.

10. Ecto-CRT was detected using Amnis Imaging Flow cytometer (EMD Millipore). 7000 events were captured per sample. Data is represented as percentage of calreticulin (CRT) positive cells with respect to the total cell population analysed. Data was plotted in Microsoft Excel as a graph.

11. Ecto-CRT expression is critical for the triggering immune pathways leading to activation of melanocyte-specific effector CD8+ T-cells. Therapeutic interventions thus require decrease in Ecto-CRT exposure on the melanocytes. Suppression of Ecto-CRT exposure on the melanocyte cell surface, as demonstrates in the FIGURE by the synthesized compounds demonstrates their ability to repress the immune activation cascade, thereby protecting melanocyte cell death in Vitiligo.

Advantages of the Invention

The present invention provides stable, easy to synthesize triazol-thiazole compounds of formula (I) which selectively suppresses the immunogenic cell death pathway and exposure of surface calreticulin in melanocytes and thus provide new treatment or prophylactic benefit options for stalling vitiligo spread.

The identification of pathway in melanocytes that can potentially sustain immunity in Vitiligo, similar to the activation pathway in cancer, can help to target the mechanisms that sustain autoimmune reactions and provide much better relief over the current treatments available in the market. This could also be of prophylactic benefit for individuals with vitiligo predisposition.

The specificity of targeting melanocytes by the compound of formula (I) and/or its derivatives would thereby prevent the side effects that are associated with traditional immune suppression.

The invention claimed is:

1. A 1,2,3 triazole-thiazole compound of formula (I);

wherein;
R is independently selected from the group consisting of alkyl, cycloalkyl, aryl, aralkyl, hydroxyalkyl and alkoxyalkyl;
n is 1, 2 or 3; and
X is a halogen;
or pharmaceutically acceptable salt thereof.

2. The compound as claimed in claim 1, wherein said compound of formula (I) is selected from the group consisting of 2-(4-Chlorophenyl)-4-((4-phenyl-1H-1,2,3-triazol-1-yl)methyl)thiazole (NDS-100971), 2-(4-Chlorophenyl)-4-((4-cyclopropyl-1H-1,2,3-triazol-1-yl)methyl) thiazole (NDS-100972), 4-((4-Butyl-1H-1,2,3-triazol-1-yl)methyl)-2-(4-chlorophenyl)thiazole (NDS-100973) 2-(4-Chlorophenyl)-4-((4-phenyl-1H-1,2,3-triazol-1-yl)methyl) thiazole (NDS-100971), 2-(4-Chlorophenyl)-4-((4-cyclopropyl-1H-1,2,3-triazol-1-yl)methyl)thiazole (NDS-100972), 4-((4-Butyl-1H-1,2,3-triazol-1-yl)methyl)-2-(4-chlorophenyl)thiazole (NDS-100973), 2-(4-Bromophenyl)-4-((4-butyl-1H-1,2,3-triazol-1-yl)methyl)thiazole, 2-(4-Fluorophenyl)-4-((4-phenyl-1H-1,2,3-triazol-1-yl)methyl) thiazole, 4-((4-Benzyl-1H-1,2,3-triazol-1-yl)methyl)-2-(4-fluorophenyl)thiazole, 4-((4-Cyclohexyl-1H-1,2,3-triazol-1-yl)methyl)-2-(4-fluorophenyl)thiazole, 4-((4-Cyclopropyl-1H-1,2,3-triazol-1-yl)methyl)-2-(4-fluorophenyl)thiazole, 2-(4-Fluorophenyl)-4-((4-propyl-1H-1,2,3-triazol-1-yl) methyl) thiazole, 2-(4-Bromophenyl)-4-((4-propyl-1H-1,2,3-triazol-1-yl)methyl)thiazole, 2-(4-Chlorophenyl)-4-((4-propyl-1H-1,2,3-triazol-1-yl)methyl)thiazole, 4-((4-Benzyl-1H-1,2,3-triazol-1-yl)methyl)-2-(4-chlorophenyl)thiazole, 2-(4-Bromophenyl)-4-((4-cyclohexyl-1H-1,2,3-triazol-1-yl) methyl)thiazole, 2-(4-Chlorophenyl)-4-((4-cyclohexyl-1H-1,2,3-triazol-1-yl)methyl)thiazole, 2-(4-Bromo phenyl)-4-((4-cyclopentyl-1H-1,2,3-triazol-1-yl) methyl)thiazole, 2-(4-Chloro phenyl)-4-((4-cyclopentyl-1H-1,2,3-triazol-1-yl) methyl) thiazole, 4-((4-Cyclopentyl-1H-1,2,3-triazol-1-yl)methyl)-2-(4-fluorophenyl)thiazole, (1-((2-(4-Fluorophenyl)thiazol-4-yl)methyl)-1H-1,2,3-triazol-4-yl)methanol, (1-((2-(4-Chlorophenyl)thiazol-4-yl)methyl)-1H-1,2,3-triazol-4-yl) methanol, (1-((2-(4-Bromophenyl)thiazol-4-yl) methyl)-1H-1,2,3-triazol-4-yl)methanol, 2-(4-Bromophenyl)-4-((4-(methoxymethyl)-1H-1,2,3-triazol-1-yl)methyl) thiazole, 2-(4-Chlorophenyl)-4-((4-(methoxymethyl)-1H-1,2,3-triazol-1-yl)methyl) thiazole, 2-(4-Fluorophenyl)-4-((4-(methoxymethyl)-1H-1,2,3-triazol-1-yl)methyl) thiazole, 2-(4-Fluorophenyl)-4-((4-(p-tolyl)-1H-1,2,3-triazol-1-yl) methyl)thiazole, 2-(4-Bromophenyl)-4-((4-(p-tolyl)-1H-1,2, 3-triazol-1-yl)methyl) thiazole, 2-(4-Chlorophenyl)-4-((4-(p-tolyl)-1H-1,2,3-triazol-1-yl)methyl)thiazole, 2-(4-Chlorophenyl)-4-(2-(4-phenyl-1H-1,2,3-triazol-1-yl)ethyl) thiazole, 2-(4-Bromophenyl)-4-(2-(4-phenyl-1H-1,2,3-triazol-1-yl)ethyl)thiazole, 2-(4-Fluorophenyl)-4-(2-(4-phenyl-1H-1,2,3-triazol-1-yl)ethyl)thiazole, 2-(4-

Chlorophenyl)-4-(2-(4-cyclopropyl-1H-1,2,3-triazol-1-yl) ethyl)thiazole, 2-(4-Bromophenyl)-4-(2-(4-cyclopropyl-1H-1,2,3-triazol-1-yl)ethyl)thiazole, 4-(2-(4-Cyclopropyl-1H-1,2,3-triazol-1-yl)ethyl)-2-(4-fluorophenyl) thiazole, (1-(2-(2-(4-Fluorophenyl)thiazol-4-yl)ethyl)-1H-1,2,3-triazol-4-yl) methanol, (1-(2-(2-(4-Bromophenyl)thiazol-4-yl)ethyl)-1H-1,2,3-triazol-4-yl)methanol, (1-(2-(2-(4-Chlorophenyl) thiazol-4-yl)ethyl)-1H-1,2,3-triazol-4-yl)methanol, 2-(4-Fluorophenyl)-4-(2-(4-(methoxymethyl)-1H-1,2,3-triazol-1-yl)ethyl)thiazole, 2-(4-Chlorophenyl)-4-(2-(4-(methoxymethyl)-1H-1,2,3-triazol-1-yl)ethyl)thiazole, 2-(4-Bromophenyl)-4-(2-(4-(methoxymethyl)-1H-1,2,3-triazol-1-yl)ethyl)thiazole, 2-(4-Bromophenyl)-4-(2-(5-(p-tolyl)-1H-1,2,3-triazol-1-yl)ethyl)thiazole, 2-(4-Fluorophenyl)-4-(2-(5-phenyl-1H-1,2,3-triazol-1-yl)ethyl)thiazole, 2-(4-Chlorophenyl)-4-(2-(5-phenyl-1H-1,2,3-triazol-1-yl)ethyl) thiazole, 2-(4-Bromophenyl)-4-(2-(5-phenyl-1H-1,2,3-triazol-1-yl)ethyl) thiazole, 2-(4-Bromophenyl)-4-(2-(5-propyl-1H-1,2,3-triazol-1-yl)ethyl)thiazole, 2-(4-Fluorophenyl)-4-(2-(5-propyl-1H-1,2,3-triazol-1-yl)ethyl) thiazole, 2-(4-Chlorophenyl)-4-(2-(5-propyl-1H-1,2,3-triazol-1-yl)ethyl)thiazole, 4-(2-(5-Cyclopropyl-1H-1,2,3-triazol-1-yl)ethyl)-2-(4-fluorophenyl)thiazole, 2-(4-Chlorophenyl)-4-(2-(5-cyclopropyl-1H-1,2,3-triazol-1-yl) ethyl)thiazole, 2-(4-Bromophenyl)-4-(2-(5-cyclopropyl-1H-1,2,3-triazol-1-yl)ethyl)thiazole, (1-(2-(2-(4-Fluorophenyl) thiazol-4-yl)ethyl)-1H-1,2,3-triazol-5-yl) methanol, (1-(2-(2-(4-Chlorophenyl)thiazol-4-yl)ethyl)-1H-1,2,3-triazol-5-yl) methanol and (1-(2-(2-(4-Bromophenyl)thiazol-4-yl) ethyl)-1H-1,2,3-triazol-5-yl)methanol.

3. A process for the preparation of 1,2,3 triazole-thiazole compound of formula (I) as claimed in claim 1, said process comprising the steps of:
(a) adding sodium azide to a solution of chloro compound in solvent followed by stirring the reaction mixture at temperature in the range of 50 to 60° C. for a period of 5 to 6 hours to afford a corresponding azido compound;
(b) adding the azido compound of step (a) to a solution of copper (II) sulfate pentahydrate, reducing agent and alkyne in a suitable solvent, followed by stirring the reaction mixture at temperature of 25 to 32° C. for a period of 5 to 6 hours.

4. The process as claimed in claim 3, wherein said chloro compound is selected from the group consisting of 4-(chloromethyl)-2-(4-chlorophenyl)thiazole, 4-(chloromethyl)-2-(4-bromophenyl)thiazole, 4-(chloromethyl)-2-(4-fluorophenyl)thiazole and 4-(chloromethyl)-2-(4-iodophenyl) thiazole.

5. The process as claimed in claim 3, wherein said azido compound is selected from the group consisting of 4-(Azidomethyl)-2-(4-chlorophenyl)thiazole, 4-(Azidomethyl)-2-(4-bromophenyl)thiazole, 4-(azidomethyl)-2-(4-fluorophenyl)thiazole and 4-(azidomethyl)-2-(4-iodophenyl)thiazole.

6. The process as claimed in claim 3, wherein said solvent is selected from the group consisting of a polar aprotic solvent, t-butanol, water or mixture thereof.

7. The process as claimed in claim 3, wherein said additive is selected from the group consisting of sodium ascorbate, 2-ethynylpyridine and triethyl amine.

8. The process as claimed in claim 3, wherein said alkyne is R—C≡CH wherein 'R' is independently selected from the group consisting of alkyl, cycloalkyl, aryl, aralkyl, hydroxyalky and alkoxyalkyl.

9. The process as claimed in claim 3, wherein said alkyne is selected from the group consisting of phenylacetylene, cyclopropylacetylene, 1-hexyne, 1-heptyne, 5-hexyn-1-ol and ethylpropiolate.

10. A pharmaceutical composition comprising compound of formula (I) as claimed in claim 1 or a pharmaceutically acceptable salt thereof and at least one pharmaceutically acceptable carrier.

11. A method for treating spread of depigmentation in vitiligo by suppressing immunogenic cell death of melanocytes and suppressing localization of calreticulin to the cell surface of melanocytes, wherein said method comprises administering to the subject a therapeutically effective amount of 1,2,3 triazole-thiazole compound of formula (I) or pharmaceutically acceptable salt thereof.

12. The method as claimed in claim 11, wherein said subject is human.

13. The process according to claim 6, wherein the polar aprotic solvent is DMF or DMPU.

* * * * *